(12) United States Patent
Stad et al.

(10) Patent No.: US 8,790,348 B2
(45) Date of Patent: Jul. 29, 2014

(54) DUAL PIVOT INSTRUMENT FOR REDUCTION OF A FIXATION ELEMENT AND METHOD OF USE

(75) Inventors: Shawn D. Stad, Fall River, MA (US); James Paiva, Warren, RI (US)

(73) Assignee: DePuy Spine, Inc., Raynham, MA (US)

( * ) Notice: Subject to any disclaimer, the term of this patent is extended or adjusted under 35 U.S.C. 154(b) by 1170 days.

(21) Appl. No.: 11/864,479

(22) Filed: Sep. 28, 2007

(65) Prior Publication Data
US 2009/0088764 A1 Apr. 2, 2009

(51) Int. Cl.
A61B 17/70 (2006.01)

(52) U.S. Cl.
USPC ........................................ 606/86 A

(58) Field of Classification Search
USPC ........... 606/86 A, 90, 99, 104, 108, 151, 208, 606/248–265, 278–279
See application file for complete search history.

(56) References Cited

U.S. PATENT DOCUMENTS

| 410,780 | A |   | 9/1889 | Cahn |
|---|---|---|---|---|
| 1,470,313 | A |   | 10/1923 | Woolen |
| 1,628,144 | A |   | 5/1927 | Herrmann |
| 1,709,766 | A |   | 4/1929 | Bolton |
| 1,889,330 | A |   | 11/1932 | Humes et al. |
| 1,925,385 | A |   | 9/1933 | Humes et al. |
| 2,113,246 | A | * | 4/1938 | Wappler ............... 606/205 |
| 2,248,054 | A |   | 7/1941 | Becker |
| 2,248,057 | A |   | 7/1941 | Bond |
| 2,291,413 | A |   | 7/1942 | Siebrandt |
| 2,370,407 | A |   | 2/1945 | McCartney |
| 2,800,820 | A |   | 7/1957 | Retterath |
| 3,960,147 | A |   | 6/1976 | Murray |
| 4,237,875 | A |   | 12/1980 | Termanini |
| 4,271,836 | A |   | 6/1981 | Bacal et al. |
| 4,411,259 | A |   | 10/1983 | Drummond |
| 4,445,513 | A |   | 5/1984 | Ulrich et al. |

(Continued)

FOREIGN PATENT DOCUMENTS

| DE | 4238339 | 5/1994 |
|---|---|---|
| DE | 29806563 U1 | 6/1998 |

(Continued)

OTHER PUBLICATIONS

International Search Report (PCT/US2008/068515) dated Jan. 2, 2009.

(Continued)

Primary Examiner — Sameh Boles
(74) Attorney, Agent, or Firm — Nutter McClennen & Fish LLP

(57) ABSTRACT

A spinal fixation element fixation reduction system is provided herein. In general, the system can include a cap element with a bore having a central axis extending therethrough wherein the cap element is configured to releasably engage any type of surgical device (e.g., an access sleeve, a vertebral body rotator, etc.). Further, the system can include a driver configured to be slidably and removably positioned through the cap element. The system can also include an actuator configured to apply a force to the driver substantially along the central axis of the cap element thereby moving the driver in a distal direction so as to effect reduction of a spinal fixation element into a bone anchor. Additionally, a method of reducing a spinal fixation element into a bone anchor is also provided wherein the method can be performed as a minimally invasive surgical procedure or as an open procedure.

20 Claims, 11 Drawing Sheets

(56) References Cited

U.S. PATENT DOCUMENTS

| | | |
|---|---|---|
| 4,655,223 A | 4/1987 | Kim |
| 4,809,695 A | 3/1989 | Gwathmey et al. |
| 4,896,661 A | 1/1990 | Bogert et al. |
| 5,014,407 A | 5/1991 | Boughten et al. |
| 5,020,519 A | 6/1991 | Hayes et al. |
| D346,217 S | 4/1994 | Sparker et al. |
| 5,306,248 A | 4/1994 | Barrington |
| 5,364,397 A | 11/1994 | Hayes et al. |
| 5,391,170 A | 2/1995 | McGuire et al. |
| 5,429,641 A | 7/1995 | Gotfried et al. |
| 5,431,658 A | 7/1995 | Moskovich |
| 5,484,440 A | 1/1996 | Allard |
| 5,545,165 A | 8/1996 | Biedermann et al. |
| 5,551,320 A | 9/1996 | Horobec et al. |
| 5,616,143 A | 4/1997 | Schlapfer et al. |
| 5,649,931 A | 7/1997 | Bryant et al. |
| 5,672,175 A | 9/1997 | Martin |
| 5,683,399 A | 11/1997 | Jones |
| 5,697,933 A | 12/1997 | Gundlapalli et al. |
| 5,707,371 A | 1/1998 | Metz-Stavenhagen et al. |
| 5,720,751 A | 2/1998 | Jackson |
| 5,725,532 A | 3/1998 | Shoemaker |
| 5,746,757 A | 5/1998 | McGuire |
| 5,782,831 A | 7/1998 | Sherman et al. |
| 5,810,878 A | 9/1998 | Burel et al. |
| 5,910,141 A | 6/1999 | Morrison et al. |
| 5,941,885 A | 8/1999 | Jackson |
| 5,951,564 A | 9/1999 | Schroder et al. |
| 5,951,579 A * | 9/1999 | Dykes ............................ 606/166 |
| 6,010,509 A | 1/2000 | Delgado et al. |
| 6,036,692 A | 3/2000 | Burel et al. |
| 6,099,528 A | 8/2000 | Saurat et al. |
| 6,123,707 A | 9/2000 | Wagner |
| 6,139,549 A | 10/2000 | Keller |
| 6,183,472 B1 | 2/2001 | Lutz et al. |
| 6,210,330 B1 | 4/2001 | Tepper et al. |
| 6,251,112 B1 | 6/2001 | Jackson |
| 6,258,090 B1 | 7/2001 | Jackson |
| 6,371,973 B1 | 4/2002 | Tepper et al. |
| 6,440,133 B1 | 8/2002 | Beale et al. |
| 6,440,142 B1 | 8/2002 | Ralph et al. |
| 6,440,144 B1 * | 8/2002 | Bacher ........................... 606/142 |
| 6,511,484 B2 | 1/2003 | Torode et al. |
| 6,530,929 B1 | 3/2003 | Justis et al. |
| 6,589,249 B2 | 7/2003 | Sater et al. |
| 6,648,888 B1 | 11/2003 | Shluzas |
| 6,660,006 B2 | 12/2003 | Markworth et al. |
| 6,726,692 B2 | 4/2004 | Bette et al. |
| 6,743,231 B1 | 6/2004 | Gray et al. |
| 6,746,449 B2 | 6/2004 | Jones et al. |
| 6,752,832 B2 | 6/2004 | Neumann |
| 6,755,829 B1 | 6/2004 | Bono et al. |
| 6,790,208 B2 | 9/2004 | Oribe et al. |
| 6,790,209 B2 | 9/2004 | Beale et al. |
| 6,827,722 B1 | 12/2004 | Schoenefeld |
| 7,081,117 B2 | 7/2006 | Bono et al. |
| 7,083,621 B2 | 8/2006 | Shaolian et al. |
| 7,156,849 B2 | 1/2007 | Dunbar et al. |
| 7,179,254 B2 | 2/2007 | Pendekanti et al. |
| 7,179,261 B2 | 2/2007 | Sicvol et al. |
| 7,278,995 B2 | 10/2007 | Nichols et al. |
| 7,320,689 B2 | 1/2008 | Keller |
| 7,371,239 B2 | 5/2008 | Dec et al. |
| 7,462,182 B2 | 12/2008 | Lim |
| 7,485,120 B2 | 2/2009 | Ray |
| 7,491,207 B2 | 2/2009 | Keyer et al. |
| 7,527,638 B2 | 5/2009 | Anderson et al. |
| 7,572,281 B2 | 8/2009 | Runco et al. |
| 7,621,918 B2 | 11/2009 | Jackson |
| 7,651,502 B2 | 1/2010 | Jackson |
| 7,666,188 B2 | 2/2010 | Anderson et al. |
| 7,708,763 B2 | 5/2010 | Selover et al. |
| 7,867,237 B2 | 1/2011 | Stad et al. |
| 7,887,541 B2 | 2/2011 | Runco et al. |
| 7,988,698 B2 | 8/2011 | Rosenberg et al. |
| 2001/0029376 A1 | 10/2001 | Sater et al. |
| 2002/0072752 A1 | 6/2002 | Zucherman et al. |
| 2002/0095153 A1 | 7/2002 | Jones et al. |
| 2003/0009168 A1 | 1/2003 | Beale et al. |
| 2003/0028195 A1 | 2/2003 | Bette |
| 2003/0083747 A1 | 5/2003 | Winterbottom et al. |
| 2003/0125750 A1 | 7/2003 | Zwimmann et al. |
| 2003/0149438 A1 | 8/2003 | Nichols et al. |
| 2003/0171756 A1 * | 9/2003 | Fallin et al. .................... 606/80 |
| 2003/0191370 A1 | 10/2003 | Phillips |
| 2003/0199872 A1 | 10/2003 | Markworth et al. |
| 2003/0225408 A1 | 12/2003 | Nichols et al. |
| 2004/0036254 A1 | 2/2004 | Patton |
| 2004/0049191 A1 | 3/2004 | Markworth et al. |
| 2004/0147936 A1 | 7/2004 | Rosenberg et al. |
| 2004/0147937 A1 | 7/2004 | Dunbar et al. |
| 2004/0172057 A1 | 9/2004 | Guillebon et al. |
| 2004/0176779 A1 | 9/2004 | Casutt et al. |
| 2004/0220567 A1 | 11/2004 | Eisermann et al. |
| 2004/0254576 A1 | 12/2004 | Dunbar et al. |
| 2004/0267275 A1 | 12/2004 | Cournoyer et al. |
| 2005/0015094 A1 | 1/2005 | Keller |
| 2005/0015095 A1 | 1/2005 | Keller |
| 2005/0033299 A1 | 2/2005 | Shluzas |
| 2005/0055031 A1 | 3/2005 | Lim |
| 2005/0059969 A1 | 3/2005 | McKinley |
| 2005/0079909 A1 | 4/2005 | Singhaseni |
| 2005/0090824 A1 | 4/2005 | Shluzas et al. |
| 2005/0131408 A1 | 6/2005 | Sicvol et al. |
| 2005/0131420 A1 | 6/2005 | Techiera et al. |
| 2005/0131421 A1 | 6/2005 | Anderson et al. |
| 2005/0131422 A1 | 6/2005 | Anderson et al. |
| 2005/0143749 A1 | 6/2005 | Zalenski et al. |
| 2005/0149036 A1 * | 7/2005 | Varieur et al. .................. 606/86 |
| 2005/0149048 A1 * | 7/2005 | Leport et al. ................... 606/99 |
| 2005/0149053 A1 | 7/2005 | Varieur et al. |
| 2005/0192570 A1 | 9/2005 | Jackson |
| 2005/0192579 A1 | 9/2005 | Jackson |
| 2005/0228392 A1 | 10/2005 | Keyer et al. |
| 2005/0261702 A1 * | 11/2005 | Oribe et al. ................... 606/103 |
| 2006/0009775 A1 | 1/2006 | Dec et al. |
| 2006/0025768 A1 | 2/2006 | Iott et al. |
| 2006/0036254 A1 | 2/2006 | Lim |
| 2006/0036260 A1 | 2/2006 | Runco et al. |
| 2006/0069391 A1 | 3/2006 | Jackson |
| 2006/0074418 A1 | 4/2006 | Jackson |
| 2006/0079909 A1 | 4/2006 | Runco et al. |
| 2006/0089651 A1 | 4/2006 | Trudeau et al. |
| 2006/0095035 A1 | 5/2006 | Jones et al. |
| 2006/0111712 A1 | 5/2006 | Jackson |
| 2006/0111713 A1 | 5/2006 | Jackson |
| 2006/0111730 A1 | 5/2006 | Hay |
| 2006/0166534 A1 | 7/2006 | Brumfield et al. |
| 2006/0166535 A1 | 7/2006 | Brumfield et al. |
| 2006/0293692 A1 | 12/2006 | Whipple et al. |
| 2007/0093849 A1 | 4/2007 | Jones et al. |
| 2007/0100347 A1 | 5/2007 | Stad et al. |
| 2007/0129731 A1 | 6/2007 | Sicvol et al. |
| 2007/0161998 A1 | 7/2007 | Whipple |
| 2007/0167954 A1 | 7/2007 | Sicvol et al. |
| 2007/0173831 A1 | 7/2007 | Abdou |
| 2007/0185375 A1 | 8/2007 | Stad et al. |
| 2007/0213722 A1 | 9/2007 | Jones et al. |
| 2007/0233097 A1 | 10/2007 | Anderson et al. |
| 2007/0260261 A1 | 11/2007 | Runco et al. |
| 2007/0270880 A1 | 11/2007 | Lindemann et al. |
| 2007/0282337 A1 | 12/2007 | Garamszegi |
| 2008/0077134 A1 | 3/2008 | Dziedzic et al. |
| 2008/0077135 A1 | 3/2008 | Stad et al. |
| 2008/0243190 A1 | 10/2008 | Dziedzic et al. |
| 2008/0255574 A1 | 10/2008 | Dye |
| 2009/0030419 A1 | 1/2009 | Runco et al. |
| 2009/0030420 A1 | 1/2009 | Runco et al. |
| 2009/0054902 A1 | 2/2009 | Mickiewicz et al. |
| 2009/0082811 A1 | 3/2009 | Stad et al. |
| 2009/0088764 A1 | 4/2009 | Stad et al. |
| 2009/0138056 A1 | 5/2009 | Anderson et al. |
| 2009/0143828 A1 | 6/2009 | Stad et al. |
| 2010/0137915 A1 | 6/2010 | Anderson et al. |

(56) References Cited

U.S. PATENT DOCUMENTS

| | | |
|---|---|---|
| 2011/0034961 A1 | 2/2011 | Runco et al. |
| 2011/0034962 A1 | 2/2011 | Dunbar, Jr. et al. |
| 2011/0093022 A1 | 4/2011 | Runco et al. |
| 2011/0144695 A1 | 6/2011 | Rosenberg et al. |
| 2012/0253413 A1 | 10/2012 | Runco et al. |

FOREIGN PATENT DOCUMENTS

| | | | |
|---|---|---|---|
| EP | 948939 A2 | 10/1999 | |
| EP | 1574175 | 9/2005 | |
| EP | 1648320 | 4/2006 | |
| EP | 1796564 | 6/2007 | |
| FR | 2680314 A1 * | 2/1993 | A61B 17/32 |
| FR | 2677242 A1 | 7/1996 | |
| FR | 2729291 A1 | 7/1996 | |
| WO | 9621396 A1 | 7/1996 | |
| WO | 2005006948 A2 | 1/2005 | |
| WO | 2006020443 A1 | 2/2006 | |

OTHER PUBLICATIONS

U.S. Patent No. 6,790,209 Reissue Application Declaration and related Transmittal Letter and Information Disclosure Statement citing schematic drawings from Sofamor, "Indroducteur—Contreur De Tige", Jan. 1, 1994.

International Search Report and Written Opinion for PCT/US2008/072851 dated Nov. 6, 2008.

International Search Report and Written Opinion mailed Nov. 6, 2008 for Application No. PCT/US2008/072851.

Extended European Search Report issued Apr. 26, 2012 for Application No. 08781067.7 (7 pages).

* cited by examiner

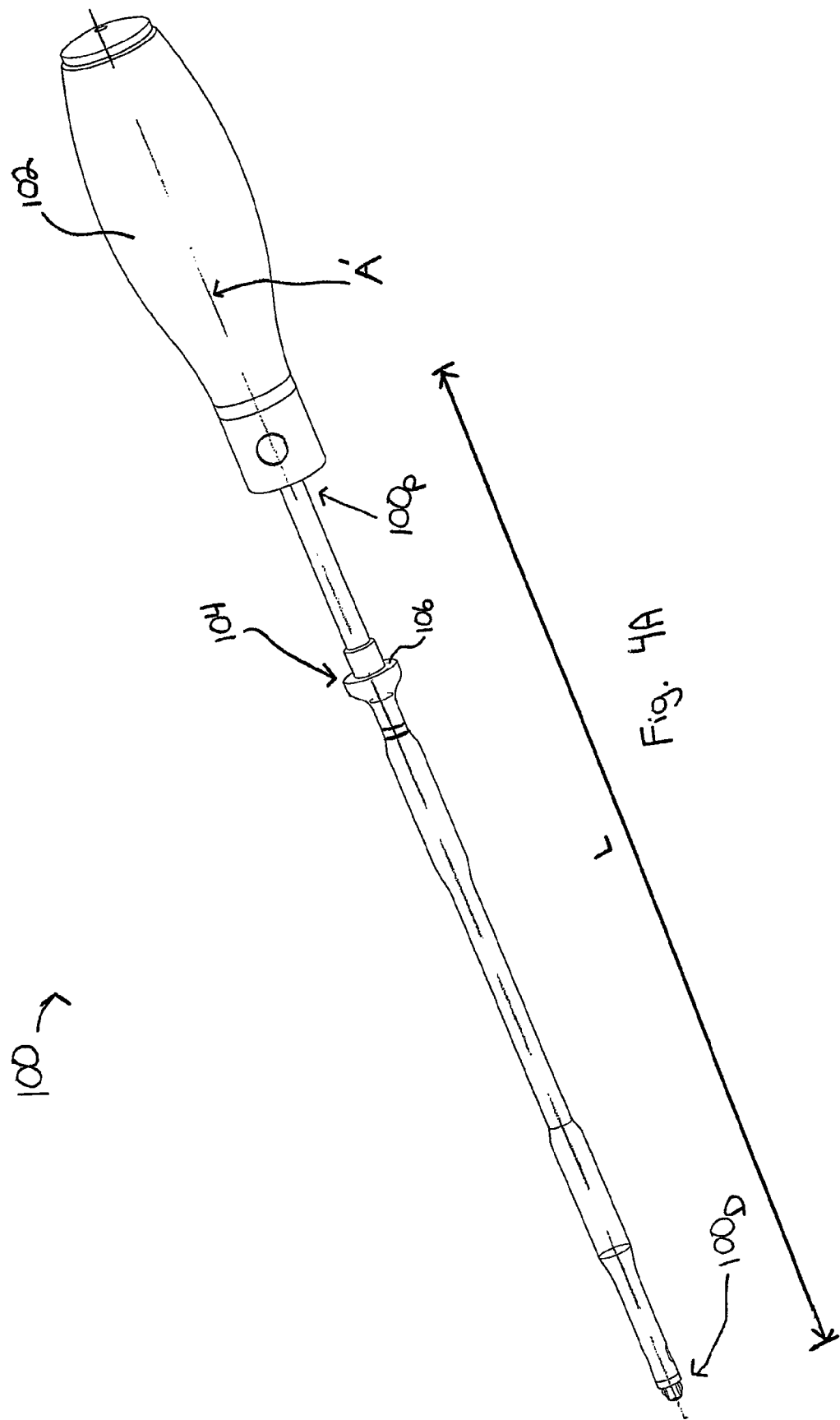

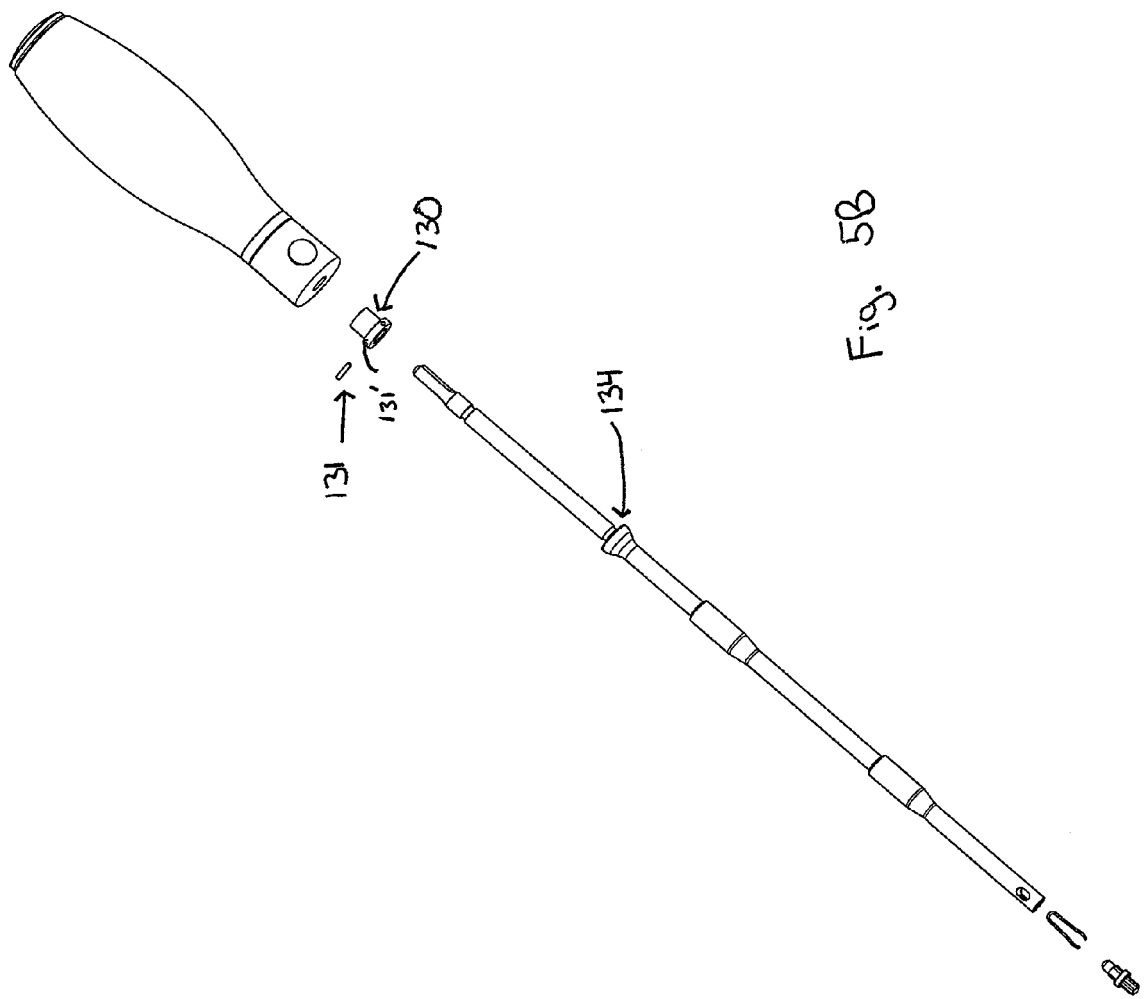

DUAL PIVOT INSTRUMENT FOR REDUCTION OF A FIXATION ELEMENT AND METHOD OF USE

FIELD OF USE

The present disclosure relates to systems and methods for reducing a spinal fixation element into a bone anchor.

BACKGROUND

Spinal fixation devices are used in orthopedic surgery to align and/or fix a desired relationship between adjacent vertebral bodies. Such devices typically include a spinal fixation element, such as a relatively rigid fixation rod, that is coupled to adjacent vertebrae by attaching the element to various anchoring devices, such as hooks, bolts, wires, or screws. The fixation rods can have a predetermined contour that has been designed according to the properties of the target implantation site, and once installed, the instrument holds the vertebrae in a desired spatial relationship, either until desired healing or spinal fusion has taken place, or for some longer period of time.

Spinal fixation devices can be anchored to specific portions of the vertebra. Since each vertebra varies in shape and size, a variety of anchoring devices have been developed to facilitate engagement of a particular portion of the bone. Pedicle screw assemblies, for example, have a shape and size that is configured to engage pedicle bone. Such screws typically include a threaded shank that is adapted to be threaded into a vertebra, and a head portion having a rod-receiving element, usually in the form of a U-shaped slot formed in the head. A set-screw, plug, or similar type of fastening mechanism, is used to lock the fixation rod into the rod-receiving head of the pedicle screw. In use, the shank portion of each screw is threaded into a vertebra, and once properly positioned, a fixation rod is seated through the rod-receiving member of each screw and the rod is locked in place by tightening a cap or other fastener mechanism to securely interconnect each screw and the fixation rod.

While current spinal fixation systems have proven effective, difficulties have been encountered in mounting rods into the rod-receiving member of various fixation devices. In particular, it can be difficult to align and seat the rod into the rod receiving portion of adjacent fixation devices due to the positioning and rigidity of the vertebra into which the fixation device is mounted. Thus, the use of a spinal rod reduction device, also sometimes referred to as a spinal rod approximator, is often required in order to grasp the head of the fixation device and reduce the rod into the rod-receiving head of the fixation device.

While several rod reduction devices are known in the art, some tend to be difficult and very time-consuming to use. Accordingly, there is a need for improved rod reduction systems and methods for seating a spinal rod, or other spinal fixation element, into one or more spinal implants or fasteners.

SUMMARY

Systems and methods for reducing a spinal fixation element into a bone anchor are provided herein. More specifically, the presently disclosed embodiments provide a modular system having a drive mechanism configured to apply a force substantially along a longitudinal axis of a driver which is slidably and removably coupled to the drive mechanism. In response to such a force, the driver can slide in a distal direction along a central axis of a surgical device (e.g., a percutaneous access device, a vertebral body rotator, etc.) thereby reducing a spinal fixation element into a bone anchor. As will be described below, the modular nature of the system allows for easy and efficient coupling of the drive mechanism to any number of drivers of different sizes and shapes. Additionally, the drive mechanism can be configured to include various pivotable connections thereby optimizing the amount of force being delivered substantially along the longitudinal axis of the driver (and along the central axis of the percutaneous axis device) thereby providing a mechanical advantage over commonly used systems and/or methods.

Various aspects of a spinal fixation element reduction system are provided herein. In one aspect, the system comprises a cap element having a proximal end and a distal end with a bore extending therethrough along a central axis thereof wherein the cap element can be sized and configured to releasably engage a surgical sleeve (e.g., a percutaneous access device, a vertebral body rotator, etc.). The system can include a first support having a proximal handle portion and a distal end pivotally coupled to the cap element. Further, the system can include an actuator pivotally attached to the first support. The actuator can include a yoke at a distal portion thereof and a grasping member at a proximal end thereof. Further, the actuator can be effective to selectively move the yoke towards the cap element. In one embodiment, the first support and the actuator can be pivotally attached at intermediate portions in a scissors-like manner. In an exemplary embodiment, the distal end of the cap element can be configured to releasably engage the percutaneous access device and the distal end can further be rotatably engaged to the proximal end of the cap element. In an exemplary embodiment, the actuator is oriented in a non-parallel manner (e.g., substantially transverse) with respect to the central axis of the cap.

In an exemplary embodiment, the system can include a driver having a distal end, a proximal end, and a length extending therebetween. The driver can be removably and slidably disposed through the bore of the cap element. As will be described below, the distal end of the driver can be configured to contact and reduce a spinal fixation element into a bone anchor. Optionally, the distal end of the driver can also be configured to releasably engage a fastening element (e.g., a set screw) such that the driver can reduce the fixation element into the bone anchor and also secure the fixation element therein by coupling the fastening element into the bone anchor (e.g., a proximal receiving head of the bone anchor) and subsequently disengaging the fastening element from the distal end of the driver. Various embodiments of the driver are also provided which include various other features. For example, in one embodiment, the driver can include at least one marking along the length thereof wherein the marking can be configured to indicate the position of the driver relative to the cap element. In use, such markings can be indicative of a depth of the distal end of the driver relative to a patient's anatomy. In one embodiment, the driver can include a rotatable flange being positioned between the cap element and the driver thereby reducing friction between the cap element and the driver as the driver is rotated so as to secure the fastening element into the bone screw. As another example, the driver can include a flange element (e.g., a yoke interface) formed along a portion thereof configured to contact a portion of the drive mechanism thereby allowing the drive mechanism to exert a force on the driver substantially along the longitudinal axis of the driver.

As indicated above, the system can include an actuator capable of applying a linear force to the driver along the central axis of the cap element. For example, in response to an actuation force, the yoke of the actuator can be pivotally moved towards the cap element. In one embodiment, the yoke can contact the flange element of the driver. While the flange element can be configured in a variety of manners, in an exemplary embodiment, the flange element includes a proximal-facing surface configured to abut the yoke as the yoke is moved towards the cap element. In an exemplary embodiment, the system can include a pivotable member coupled to an inner surface of the yoke wherein the pivotable member can be configured to remain substantially flush against the proximal-facing surface of the flange element as the yoke moves towards the cap element thereby providing numerous benefits such as reducing dissipation of the applied force as well as reducing any wear or damage to the yoke or the flange element of the driver.

Various embodiments of an actuator of the drive mechanism are also provided herein. In an exemplary embodiment, the actuator can include a biasing mechanism in communication with the proximal handle portion of the first support and also in communication with the grasping member thereby biasing the proximal handle portion away from the grasping member. While the biasing mechanism can include virtually any type of such mechanism, in an exemplary embodiment, the biasing mechanism includes a first prong (e.g., a leaf spring) extending from the proximal handle portion of the first support and a second prong (e.g., a leaf spring) extending from the grasping member wherein a distal portion of the first prong is configured to engage a distal portion of the second prong. Optionally, the actuator can include a locking mechanism configured to maintain a position of the proximal handle portion of the first support relative to a position of the grasping member. Like the biasing mechanism, the locking mechanism can also include virtually any type of mechanism capable of controlling the position of the proximal handle portion of the first member relative to the grasping member. For example, the locking mechanism can include an elongate member having a proximal end pivotally coupled to the proximal handle portion of the first support and having a distal end which includes at least one pawl configured to releasably engage a notch or groove formed in the grasping member. In other embodiments, the locking mechanism can include a plurality of teeth or pawls formed along the length of the elongate member thereby allowing for incremental changes in position of the proximal handle portion of the first support relative to the grasping member.

In another aspect, a system is provided which includes a modular spinal fixation element reduction system comprising a drive mechanism having a cap element with a bore extending therethrough having a central axis wherein the cap element is configured to releasably engage a proximal portion of a surgical sleeve. Further, the system includes a driver that is configured to be removably and slidably disposed through the bore of the cap element wherein the drive mechanism is effective to deliver a force to the driver along the central axis of the cap element thereby causing the driver to slide distally from a first position to a second position. As described above, the driver can include a distal end which is effective to contact a spinal fixation element and upon distal movement of the driver along the central axis, seat the spinal fixation element within a bone anchor. Optionally, the system can further include a fastening element removably attached to the distal end of the driver and configured to lock a spinal fixation element within a bone anchor.

Various embodiments of such a drive mechanism are provided herein. For example, as described above, the drive mechanism can include a first support having a proximal handle portion and a distal portion pivotally coupled to the cap element. Further, the drive mechanism can include an actuator being pivotally engaged to the first support such that a yoke element formed at a distal end of the actuator resides at a biased position above the cap element. Further, the actuator can also be configured to allow the yoke element to pivotally move towards the cap element in response to an actuation force.

The driver can also include a yoke interface (e.g., a flange element) formed on a portion thereof wherein the yoke interface is configured to contact the yoke as the yoke pivotally moves toward the cap element. While the yoke interface can include virtually any configuration capable of being acting upon by the yoke, in an exemplary embodiment the yoke interface is a flange element having a substantially planar proximal facing surface. Optionally, the yoke can further include a pivotable member coupled to an inner surface of the yoke such wherein the pivotable member can be configured to remain substantially flush with the substantially planar proximal facing surface of the yoke interface as the yoke pivots toward the cap element.

Various aspects of a method for reducing a spinal fixation element into a bone anchor are also provided herein. In one aspect, a method for reducing a spinal fixation element into a bone anchor is provided which includes attaching a drive mechanism to a surgical sleeve (e.g., a percutaneous access device, vertebral body rotator, etc.) and removably coupling a driver to the drive mechanism such that the driver extends into the surgical sleeve. Thereafter, the drive mechanism can be attached to apply a force to the driver causing the driver to contact a spinal fixation element and to slide linearly and along a central axis in a distal direction of the surgical sleeve thereby reducing the spinal fixation element into a bone anchor. In an exemplary embodiment, the attaching step can further include rotatably attaching the drive mechanism to the surgical sleeve. Optionally, the method can further include releasably engaging a fastening element to a distal end of the driver, coupling the fastening element to a proximal portion of the bone anchor, and disengaging the fastening element from the distal portion of the driver. Also, the method can be configured such that the attaching, coupling, and actuating steps summarized above (or at least one such step) can be performed as a minimally invasive surgical procedure. Alternatively, any of these steps (or all) can be performed as an open surgical procedure.

In another aspect, a method for reducing a spinal fixation element into a bone anchor is provided which includes removably attaching a cap element to a proximal portion of a percutaneous access device having a central axis extending therethrough wherein the cap element includes a bore with a central axis which is substantially collinear with the central axis of the percutaneous axis device. The cap element can further be pivotally coupled to a distal portion of a first support wherein the first support is pivotally coupled to an actuator in a scissors-like manner. The method can further include removably coupling a driver to the actuator such that the driver extends through the bore of the cap element along the central axis of the bore and resides at least partially disposed within the percutaneous access device. Like above, the driver can include a yoke interface formed along a portion thereof. The method can also include positioning a yoke formed on a distal portion of the actuator above the cap element. Additionally, the method can include supplying an actuation force to the actuator to move the yoke towards the cap element such that the yoke contacts the yoke interface of the driver to cause the driver to slide linearly and along the central axis in a distal direction of the percutaneous access device thereby reducing a spinal fixation element into a bone anchor.

These aspects, as well as others, are described in detail below.

BRIEF DESCRIPTION OF THE DRAWINGS

The systems and methods disclosed herein will be more fully understood from the following detailed description taken in conjunction with the accompanying drawings, in which:

FIG. 4A is a perspective view of an exemplary embodiment of a driver;

FIG. 5B is an exploded view of the driver of FIG. 5A;

DETAILED DESCRIPTION

Certain exemplary embodiments will now be described to provide an overall understanding of the principles of the structure, function, manufacture, and use of the systems and methods disclosed herein. One or more examples of these embodiments are illustrated in the accompanying drawings. Those skilled in the art will understand that the systems and methods specifically described herein and illustrated in the accompanying drawings are non-limiting exemplary embodiments and that the scope of the present disclosure is defined solely by the claims. The features illustrated or described in connection with one exemplary embodiment may be combined with the features of other embodiments. Such modifications and variations are intended to be included within the scope of the present disclosure.

Various embodiments of a system and method for reducing a spinal fixation element into a bone anchor are provided herein. In general, the various embodiments provide an easy and efficient system and method of coupling a drive mechanism to various types and sizes of drivers. For example, the driver can be coupled to the drive mechanism by slidably and removably positioning the driver through a bore of a cap element of the drive mechanism. Following a successful reduction, the driver is removed from the drive mechanism and the procedure can be repeated at a distinct anatomical location. Additionally, the drive mechanism can be configured to concentrate an applied linear force along a longitudinal axis of the driver thereby sliding the driver in a distal direction. Thus, minimal force is dissipated or wasted while reducing the spinal fixation element into a bone anchor. Additionally, a mechanical advantage supplied by the presently disclosed system can be further enhanced by incorporating various pivotable members into a drive mechanism of the system such that a portion of the drive mechanism in contact with the driver can pivot with the driver during application of the linear force thereby reducing any dissipation of such force and also reducing any wear or damage to the components of the system.

Figure 1:
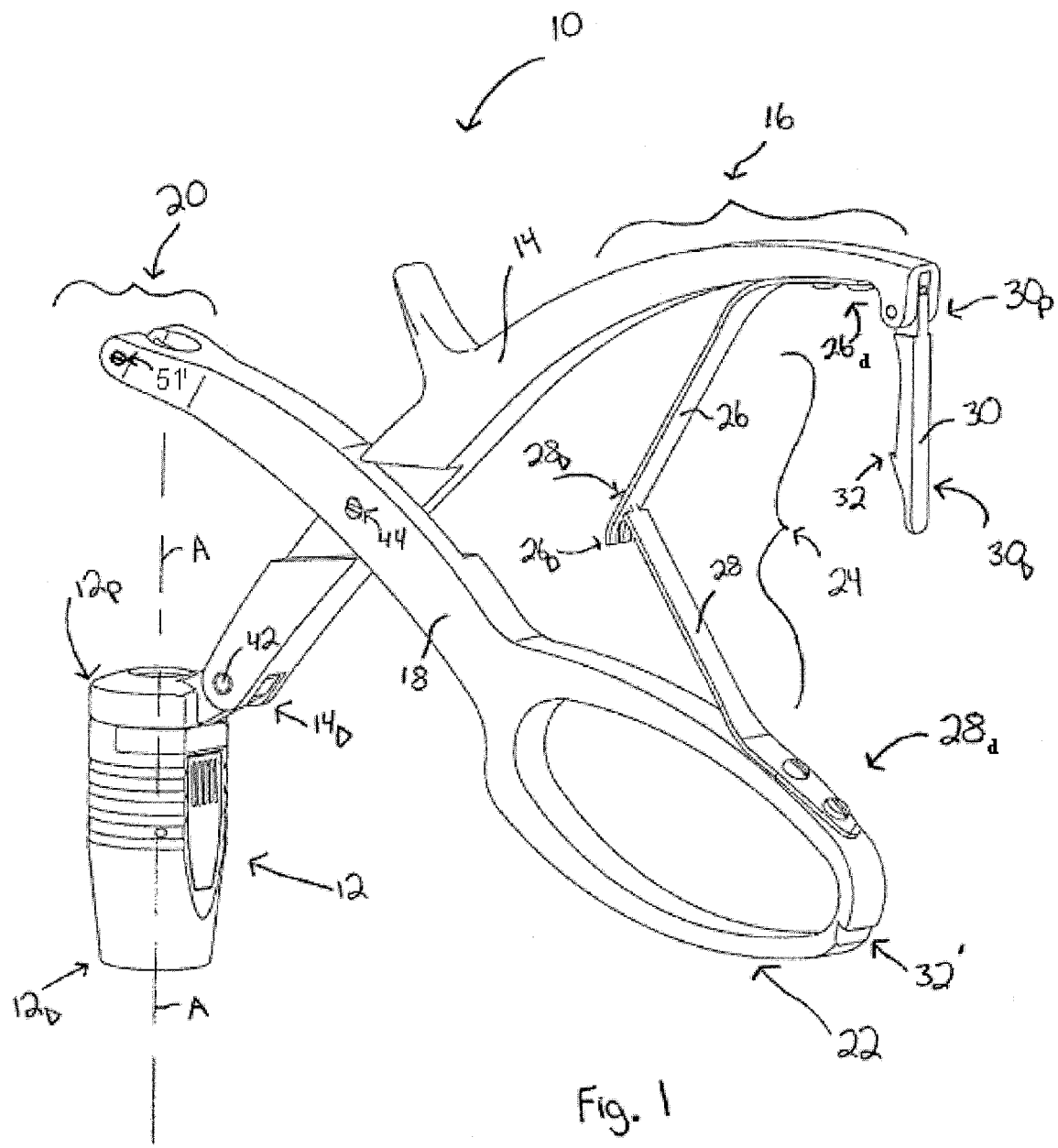
FIG. 1 is a perspective view of an exemplary embodiment of a drive mechanism.

FIG. 1 shows an exemplary embodiment of a drive mechanism 10. As an overview, the drive mechanism 10 can include a cap element 12 configured to releasably engage a proximal portion of a surgical sleeve or surgical device engaged to a vertebra (e.g., a percutaneous access device, a vertebral body rotator, etc.). Further, the drive mechanism 10 can include a first support 14 having a proximal handle portion 16 and being coupled to the cap element 12 at a distal end $14_D$ thereof. Further, the drive mechanism 10 can include an actuator 18 having a yoke 20 at a distal end and a grasping member 22 formed at a proximal portion thereof. In an exemplary embodiment, the actuator 18 is pivotably coupled to the first support 14 at a pivot point 44, which may be at an intermediate location of the actuator 18 and the first support 14, in a scissors-like manner. Thus, in response to an actuation force being applied to the actuator 18 (e.g., the handle portion 16 of the first member 14 being pivotally moved towards the grasping member 22), the yoke 20 can be driven towards the cap element 12 which enables the yoke 20 to contact a driver disposed through the cap element 12 thereby resulting in reduction of a spinal fixation element into a bone anchor. The actuator 18 can also include a biasing mechanism 24 extending between the proximal handle portion 16 of the first support 14 and the grasping member 22 to bias the handle portion 16 and the grasping member 22 apart from each other. The actuator 18 can also include a locking mechanism 30 configured to maintain a position of the proximal handle portion 16 relative to the grasping member 22.

Figure 2:
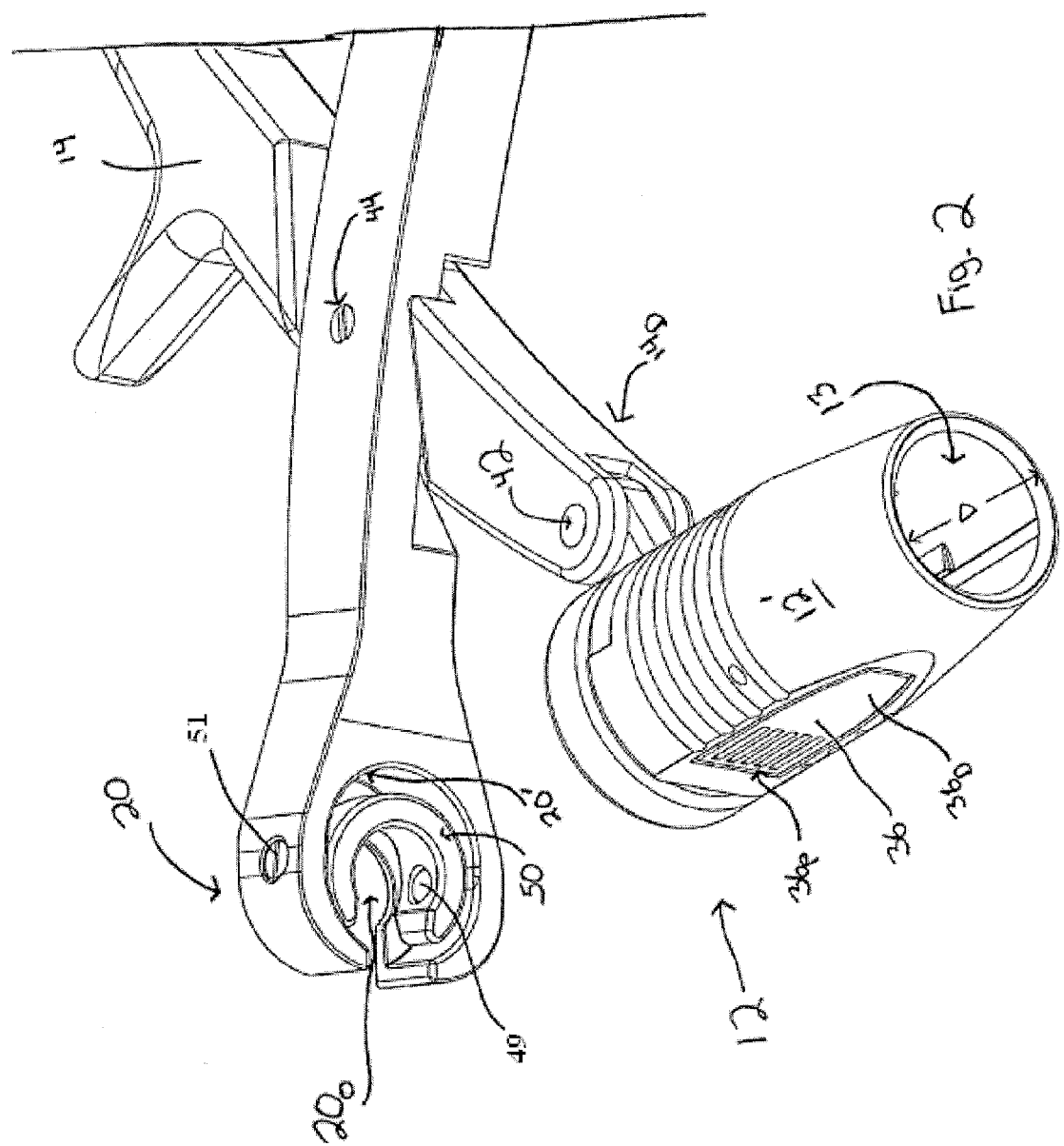
FIG. 2 is a perspective view of a distal portion of the drive mechanism of FIG. 1.
Figure 3:
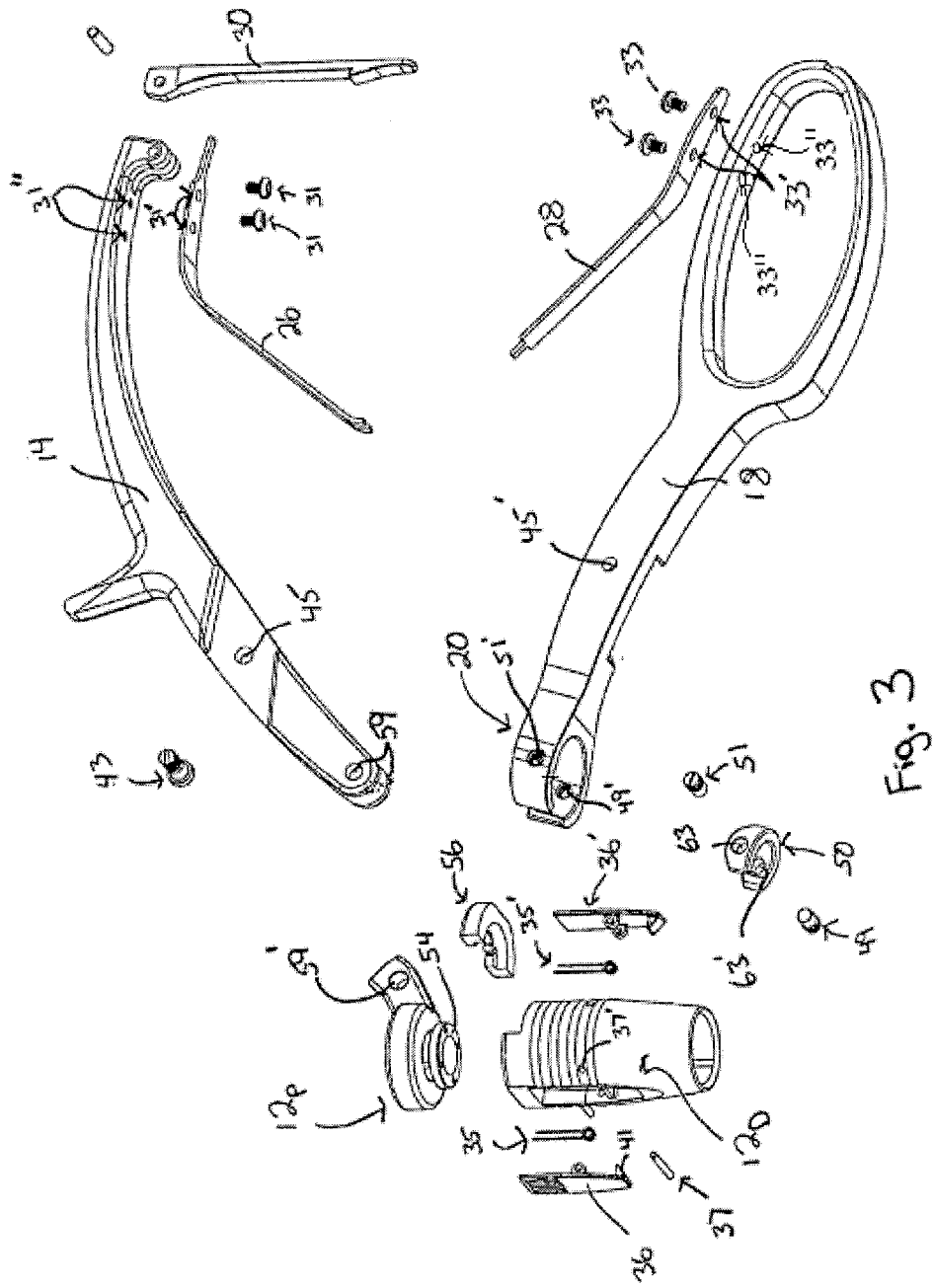
FIG. 3 is an exploded view of the drive mechanism of FIG. 1.

FIGS. 1-3 provide an exemplary embodiment of a cap element 12 of the drive mechanism 10. In general, the cap mechanism 12 can include any element being sized and configured to releasably engage a surgical sleeve (e.g., a percutaneous access device) and also having a bore extending therethrough which is configured to allow a driver (see FIGS. 4A-5B) to slidably pass therethrough. Thus, in an exemplary embodiment, the cap element 12 includes a proximal end $12_P$, a distal end $12_D$, and a bore extending therebetween having a central axis (A). The bore can be sized and configured to allow a driver (see FIG. 4A) to be slidably and removably disposed therethrough such that a longitudinal axis of the driver is substantially collinear with the central axis (A) of the bore.

Referring to FIGS. 2-3, the cap element 12 can include a distal opening 13 having a diameter (D) sized and configured to receive a proximal end of a surgical sleeve (e.g., a percutaneous access device). As the cap element 12 is advanced distally over the proximal portion of, for example, the percutaneous access device (see FIG. 6A-6D), the cap element 12 can be configured to releasably engage the proximal portion of the percutaneous access device. As will be apparent to those skilled in the art, the cap element 12 can be configured in various manners so as to releasably engage the percutaneous access device. For example, as shown, the cap element 12 can include at least one (shown as two) biased lever elements 36 coupled to a housing 12' of the cap element 12. In use, a protrusion 41 formed on a distal portion $36_D$ of the lever 36 can snap into a corresponding opening (opening 41' shown in FIG. 6A) in the proximal end of the percutaneous access device thereby releasably engaging the cap element 12 to the percutaneous access device. To release this connection, a user can compress a proximal portion $36_p$ of the lever 36 thereby rotating the lever 36 about a central fulcrum 37 disposed in corresponding holes 37' which removes the protrusion 41 from the opening of the percutaneous access device. As will be apparent to those skilled in the art, such levers 36 can be biased as such in virtually any manner capable of providing the desired effect. As shown in FIG. 3, a spring element 35, 35' can be coupled to each lever 36, 36' thereby biasing each lever 36, 36' in the desired orientation.

In an exemplary embodiment, the cap element 12 can be configured such that the proximal portion $12_P$ of the cap element 12 is rotatably coupled to the distal portion $12_D$ of the cap element 12. In such an embodiment, the distal portion $12_D$ of the cap element 12 can be configured to releasably engage the percutaneous access device thereby allowing the remainder of the drive mechanism 10 to rotate relative to the distal portion $12_D$ and to the percutaneous access device and a driver disposed therethrough. In use, such a rotatable coupling can facilitate a surgeon's ability to engage the cap element 12 to the percutaneous access device, couple the drive mechanism 10 to a driver, and/or to supply an actuation force to the actuator 18. As apparent to those skilled in the art, such a rotatable coupling can be provided in virtually any such manner capable of providing the desired effect. For example, as illustrated in the exemplary embodiment of FIG. 3, the proximal end $12_P$ of the cap element 12 can include a rotatable member 54 that is coupled to the distal portion $12_D$ of the cap element 12 via a connector 56 thereby allowing the distal end $12_D$ of the cap element 12 to rotate relative to the proximal end $12_P$ of the cap element 12. Further, the proximal portion $12_P$ of the cap element 12 can be indexed (e.g., secured via a snap-fit every 90°) relative to the distal portion $12_D$ of the cap element 12 thereby indicating a relative position of the proximal end $12_P$ to the distal end $12_D$ during rotation.

The system further includes a first support 14 having a proximal handle portion 16 and a distal end $14_D$ coupled to the cap element 12. The cap element 12 can be coupled to the distal end $14_D$ of the first support 14 by virtually any manner or mechanism known to those skilled in the art. In one embodiment, the distal end $14_D$ of the first support 14 can be rigidly engaged to the cap element 12. However, in an exemplary embodiment, the distal end $14_D$ of the first support 14 can be pivotally coupled to the cap element 12 at a pivot point 42. As will be described below, such a pivotable coupling can focus an applied force along a longitudinal axis of a driver thereby optimizes a mechanical advantage provided by the drive mechanism 10. It will be apparent to those skilled in the art that various mechanisms and/or coupling can be utilized so as to pivotally couple the cap element 12 to the distal end $14_D$ of the first support 14. For example, as shown in FIG. 3, the distal end $14_D$ of the first support 14 can include first and second openings 59 which can be configured to be aligned and positioned on opposite sides of an opening 59' formed in the proximal portion $12_P$ of the cap element 12. Once aligned as such, a set screw or pin (not shown) can be secured through the openings 59, 59' thereby securing the cap element 12 to the distal end $14_D$ of the first support 14 while also allowing for the cap element 12 to pivot at a pivot point 42 relative to the first support 14.

The system can further include an actuator 18 configured to cooperate with the first support 14 to apply a linear force substantially along a longitudinal axis of a driver that is slidably and removably disposed through the cap element 12. As described below, the application of such force can effectively reduce a spinal fixation element into a corresponding bone anchor. In general, the actuator 18 can be any mechanism capable of applying such a linear force to the driver wherein the force is supplied substantially along the longitudinal axis of the driver and also substantially along the central axis (A) of the cap element 12 thereby sliding the driver distally from a first location to a second location so as to provide the desired reduction procedure. Various aspects of such an actuator of the drive mechanism are described below.

FIGS. 1-3 provide an exemplary embodiment of an actuator 18 configured for use with the presently disclosed system. As shown, the actuator 18 can include a yoke 20 formed at a distal end thereof and a grasping member 22 formed at a proximal end. The actuator 18 can be coupled to the first support 14 at various locations, in various manners, to provide various configurations. However, in an exemplary embodiment, the actuator 18 can be coupled to the first support 14 at an intermediate location (e.g., pivot point 44) in a scissors-like manner. Similar to the pivotal coupling of the cap element 12 to the distal end $14_D$ of the first support 14, the actuator 18 can be pivotably coupled to the first member 14 in virtually any manner capable of providing the desired effect. For example, as shown, the actuator 18 can include an opening 45' along at an intermediate location thereof, and the first support 14 can also include a corresponding opening 45 at a corresponding intermediate location thereof. Once positioned as such, another set screw 43 can be disposed through the corresponding openings 45, 45' thereby securing the actuator 18 to the first support 14 while also allowing for the first support 14 to pivotally move relative to the actuator 18. In other embodiments, the actuator can be configured in a trigger configuration, a trigger-like configuration, or any other such configuration capable of forcing the yoke element into contact with a driver coupled to the drive mechanism.

As indicated, the actuator 18 can include a yoke 20 formed at a distal end thereof that is configured to exert a downward, linear force on a driver disposed in the yoke and extending through a bore of the cap element 12. More specifically, during actuation of the actuator 18, the yoke 20 can be pivotally moved towards the cap element 12 and can be configured to contact a portion of a driver thereby reducing a spinal fixation into a bone anchor. As will be apparent to those skilled in the art, the yoke 20 can be of virtually any shape, size, and/or configuration capable of contacting the driver as the yoke 20 pivotally moves towards the cap element 12 thereby applying the desired downward force to the driver. In an exemplary embodiment, the yoke 20 can be in the form of a C-shaped element having a central opening $20_O$ sized and configured to receive a driver such that, as shown in FIG. 6C, the driver can extend through the central opening $20_O$ of the yoke 20. Also, the yoke 20 can be sized and configured to engage (e.g., abut) a portion of the driver (e.g., a yoke interface, discussed below) as the yoke 20 is pivotally moved towards the cap element 12.

In an exemplary embodiment, the yoke 20 can be configured to remain substantially flush with a portion of a driver as the yoke 20 pivotally moves toward the cap element 12 thereby optimizing the mechanical advantage provided by the drive mechanism 10 while also reducing any amount of wear and/or damage to the driver and/or yoke 20. As will be appreciated by those skilled in the art, the yoke 20 can be configured in various manners to allow for such a flush contact between the yoke element and a corresponding portion of the driver (e.g., a yoke interface, described in greater detail below). For example, in one embodiment, a pivotable member 50 can be coupled to an inner surface 20' of the yoke 20 such that the pivotable member 50 can pivot with a corresponding portion of a driver as the yoke 20 pivotally moves towards the cap element 12. Similar to the yoke 20 itself, the pivotable member 50 can also have various sizes and/or configurations. Referring to FIG. 2, the pivotable member 50 can be also configured as a C-shaped element being sized and configured to receive a driver. As will be appreciated by those skilled in the art, the pivotable member 50 can be coupled to the yoke 20 in virtually any manner capable of allowing the member 50 to pivot as described above. For example, as detailed in FIG. 3, the pivotable member 50 can include a first opening 63 and a second opening 63' corresponding to first 51' and second openings 49' formed in the yoke 20. Thus, a first set screw 51 can be disposed within the first set of corresponding openings 63, 51' and a second set screw 49 can be disposed through the second set of corresponding openings 63', 49' thereby providing the desired pivot functionality while also securing the pivotable member 50 to the yoke 20.

The actuator 18 can also include a biasing mechanism 24 configured to maintain the yoke 20 at a first, biased location relative to (e.g., above) the cap element 12. As will be described, in response to the application of an actuation force sufficient to overcome the biasing force, the yoke 20 will move from the biased position (e.g., as shown in FIG. 6C) to an unbiased position (e.g., as shown in FIG. 6D) thereby moving the yoke 20 towards the cap element 12 and thus into contact with a portion of a driver. As will be apparent to those skilled in the art, the biasing mechanism 24 can include any mechanism at any location of the drive mechanism that is capable of providing the desired effect. In an exemplary embodiment, the biasing mechanism 24 can be in communication with the proximal handle portion 16 of the first support 14 and also in communication with the grasping member 22 of the actuator 18 thereby applying a biasing force which is configured to push these elements 16, 22 apart from one another. In other embodiments, the biasing mechanism 24 can be in communication with the first support 14 and the actuator 18 at a distal position relative to an engagement point 44 between the first support 14 and actuator 18.

In one embodiment, the biasing mechanism 24 can include at least one spring or spring-like element (not shown) in communication with the proximal handle portion 16 of the first support and the grasping member 22, a ratcheting mechanism (not shown) in communication with such elements 16, 22, any type(s) of non-compliant material configured in various manners to provide the desired effect on the handle portion 16 and grasping member 22, etc. In the illustrated exemplary embodiment, the biasing mechanism 24 can include a first prong 26 (e.g., a leaf spring) extending from the handle portion 16 and a second prong 28 (e.g., a leaf spring) extending from the grasping member 22 wherein a distal end $26_D$ of the first prong 26 is configured to receive a distal end $28_D$ of the second prong 28. In such an embodiment, the prongs 26, 28 can be formed of any type(s) of non-compliant material(s) capable of exerting a force on each other such that the proximal handle portion 16 and the grasping member 18 are forced apart from one another. Those skilled in the art will appreciate that the prongs 26, 28 can be engaged or formed on respective handle portion 16 or grasping member 22 in various manners. For example, as shown, the first prong 26 can be engaged to the handle portion 16 by at least one set screw 31 disposed through a corresponding number of holes 31' in a distal end $26_d$ of the prong 26 and secured in a corresponding opening 31" formed in the first support 14. Likewise, the second prong 28 can be engaged to the grasping member 22 by at least one set screw 33 disposed through a corresponding number of holes 33' in a distal end $28_d$ of the prong 28 and secured in a corresponding openings 33" formed in the grasping member 22. In other embodiments, the prongs 26, 28 can be welded into position.

The drive mechanism 10 can also include a locking mechanism configured to maintain the position of the proximal handle portion 16 relative to the position of the grasping member 22 and therefore maintaining the position of the yoke 20 relative to the cap element 12. Like the biasing mechanism 24, the locking mechanism can include virtually any type of mechanism disposed at virtually any location of the drive mechanism 10. In the illustrated exemplary embodiment, the locking mechanism can include an elongate member 30 having a proximal portion $30_P$ extending from the proximal handle portion 16 and having a distal end $30_D$ configured to releasably engage the grasping member 22. As will be apparent to those skilled in the art, the distal portion $30_D$ of the elongate member 30 and/or the grasping member 22 can be configured in various manners to provide such a releasable engagement. For example, the distal portion $30_D$ of the elongate member 30 can include a protrusion, such as a pawl 32, capable of releasably engaging a groove 32' formed in the grasping member 22. In other embodiments, the elongate member 30 can include a plurality of such protrusions (not shown) incorporated along any desired length of the elongate member thereby allowing the position of the proximal handle portion 16 to be locked relative to the position of the grasping member 22 at various stages. Similarly, the grasping member can include a plurality of grooves. In another embodiment, the locking mechanism can include a speed-nut element configured to abut either the grasping member 22 of the proximal handle portion as the handle 16 and member 22 move towards one another.

Figure 4B:
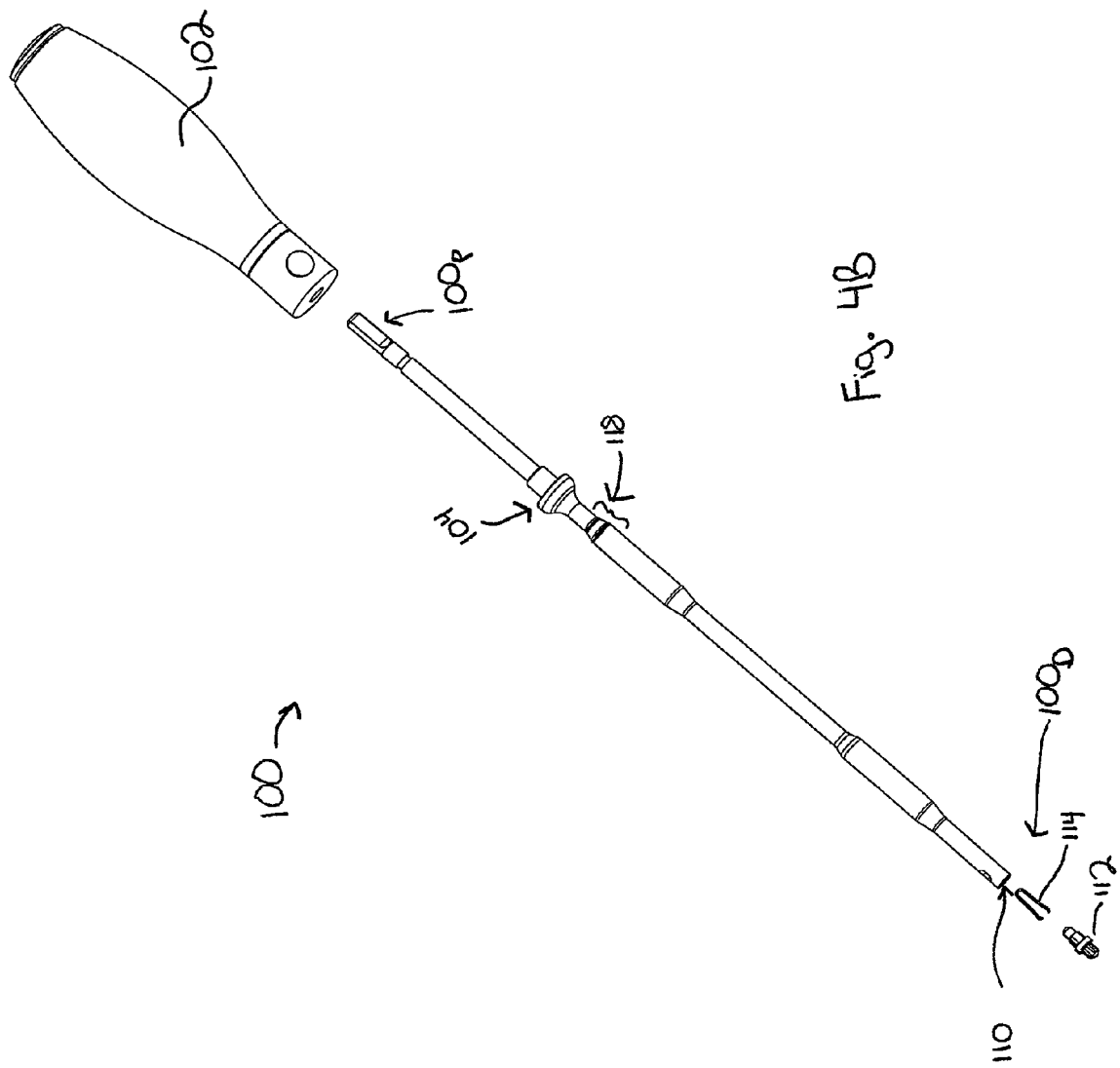
FIG. 4B is an exploded view of the driver of FIG. 4A.

In addition to the various embodiments of a drive mechanism 10 described above, the system can also include a driver 100 configured to be slidably and removably disposed in the yoke to extend through a cap element 12 of the drive mechanism 10 such that a longitudinal axis (A') of the driver 100 is substantially collinear with the central axis (A) of a bore of the cap element 12. Once so positioned, the drive mechanism 10 can apply a force to the driver 100 substantially along the central axis (A) of the cap element 12 thereby optimizing the mechanical advantage provided by the drive mechanism 10. FIGS. 4A-4B provide an exemplary embodiment of a driver 100. As shown, the driver 100 can include a proximal end $100_P$, a distal end $100_D$, and a length (L) therebetween which can be selected in light of the requirements of the surgical procedure and/or the patient's anatomy. As shown in FIG. 4B, the proximal end $100_P$ of the driver 100 can be configured to releasably engage a handle 102 configured to facilitate a user's ability to manipulate the driver 100. For example, the use of such a handle 102 can facilitate a user's ability to rotate the driver 100 which, as described in detail below, can allow the distal end $100_D$ of the driver 100 to reduce a fixation element into a bone anchor and/or engage a fastening element to the bone anchor following such reduction. As will be apparent to those skilled in the art, the handle 102 can be releasably engaged to the proximal portion $100_P$ of the driver 100 in virtually any manner capable of providing the desired effect. In another embodiment, a handle portion 102 can be welded onto the proximal portion $100_P$. In yet another embodiment, the driver 100 does not include any type of handle portion.

The distal end $100_D$ of the driver 100 can also be configured in various manners to provide various functions. For example, in an exemplary embodiment, the distal end $100_D$ can be configured to contact and manipulate a spinal fixation element disposed between the distal end $100_D$ and a bone anchor such that in response to an actuation force supplied by the drive mechanism 10 (as described above), the distal end $100_D$ of the driver 100 can effectively reduce the spinal fixation element into the corresponding bone anchor. Referring again to FIG. 4B, the distal portion $100_D$ of the driver 100 can include a flange-like element 112 coupled within a distal opening 110 via a connector 114. In an exemplary embodiment, the flange-like element 112 can be welded into position once disposed within the distal opening 110. In another embodiment, the distal end $100_D$ of the driver is a single piece which extends to the proximal end $100_P$ of the driver 100.

In another exemplary embodiment, the distal end $100_D$ of the driver 100 can be configured to releasably engage a fastening element (e.g., a set screw or pin). Thus, in such an embodiment, after reducing the spinal fixation element into a bone anchor, the driver 100 can be configured to secure a fastening element to a proximal portion of the bone anchor and subsequently disengage the fastening element from the distal end $100_D$ of the driver 100 thereby securing the fastening element within the bone screw. As will be apparent to those skilled in the art, various such techniques can be utilized to releasably engage the fastening element to the distal end $100_D$ of the driver 100.

As described above, the driver 100 can also include a yoke interface 104 configured to abut the yoke 20 as the yoke 20 pivotally moves toward the cap element 12. Those skilled in the art will appreciate that such a yoke interface 104 can be sized and configured in virtually any manner capable of contacting the yoke 20 as described above. It will also be appreciated that the yoke interface 104 can be formed along any location of the driver 100 capable of providing the desired effect. In the exemplary embodiment, shown in FIG. 4A, the yoke interface 104 is a flange element formed on the driver 100. More specifically, the flange element 104 can include a substantially flat proximal-facing surface 106 capable of receiving the yoke 20 as the yoke 20 is pivotally moves towards the cap element 12. In another embodiment, the yoke interface can be formed as ball and the yoke can be configured as a socket-type element thereby providing a ball-in-socket type engagement. As described above, in an exemplary embodiment, the substantially flat proximal-facing surface 106 of the flange element 104 can receive the pivotable member 50 coupled to the inner surface 20' of the yoke 20 such that the pivotable member 50 can remain substantially flush against the surface 106 as the force is supplied to the driver 100.

Figure 5A:
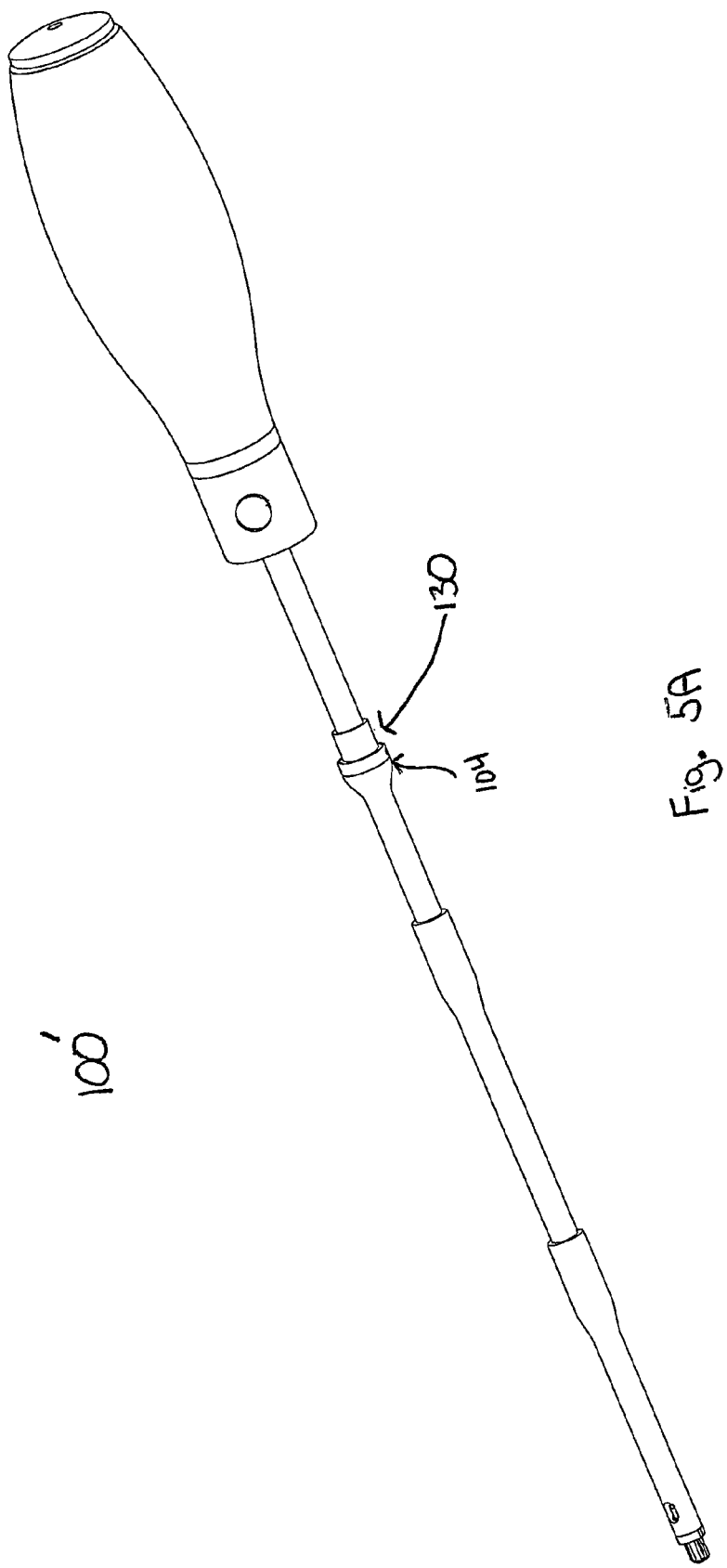
FIG. 5A is a perspective view of an another exemplary embodiment of a driver.

The driver 100 can also include various other features capable of optimizing a surgical procedure. For example, the driver 100 can include at least one or a plurality of markings 118 which can be indicative of a depth of a distal end $100_D$ of the driver 100 relative to a patient's anatomy or indicative to the position of the driver 100 relative to the cap element 12. In another exemplary embodiment shown in FIGS. 5A and 5B, the driver 100' can include a rotatable flange element 130 positioned adjacent and proximal to the yoke interface 104. In such an embodiment, the rotatable flange 130 can reduce rotational friction as the driver 100' is rotated in order to, for example, secure a fastening element to a bone anchor. As will be apparent to those skilled in the art, such a rotation flange 130 can be rotatably coupled to the driver 100' in virtually any manner capable of providing the desire effect. For example, as shown in FIG. 5B, the flange 130 can include an opening 131' configured to receive a set screw 131 such that a distal portion of the set screw 131 can be disposed in a groove 134 extending along an outer circumference of the driver 100' thereby allowing the driver 100' to rotate relative to the flange 130.

Various embodiments of a method for reducing a spinal fixation element into a bone anchor are also provided herein. In general, the method can include releasably engaging a drive mechanism to some type of surgical sleeve (e.g., a percutaneous access device, a bone anchor, a vertebral body rotator, etc.), slidably and removably coupling a driver to the drive mechanism and the surgical sleeve, and actuating an actuator of the drive mechanism so as to apply a force to a driver along a central axis of the cap element thereby reducing a spinal fixation element into the bone anchor. The method can be configured for use in minimally invasive surgical procedures (e.g., with the use of percutaneous access devices) or the method can be configured for use in open procedures (e.g., with the use of a vertebral body rotator). In some embodiments, the method can also include releasably engaging a fastening element to a distal end of a driver, securing such the fastening element to a bone anchor, and disengaging the fastening element from the distal end of the driver thereby securing the spinal fixation element within the bone anchor.

Figure 6A:
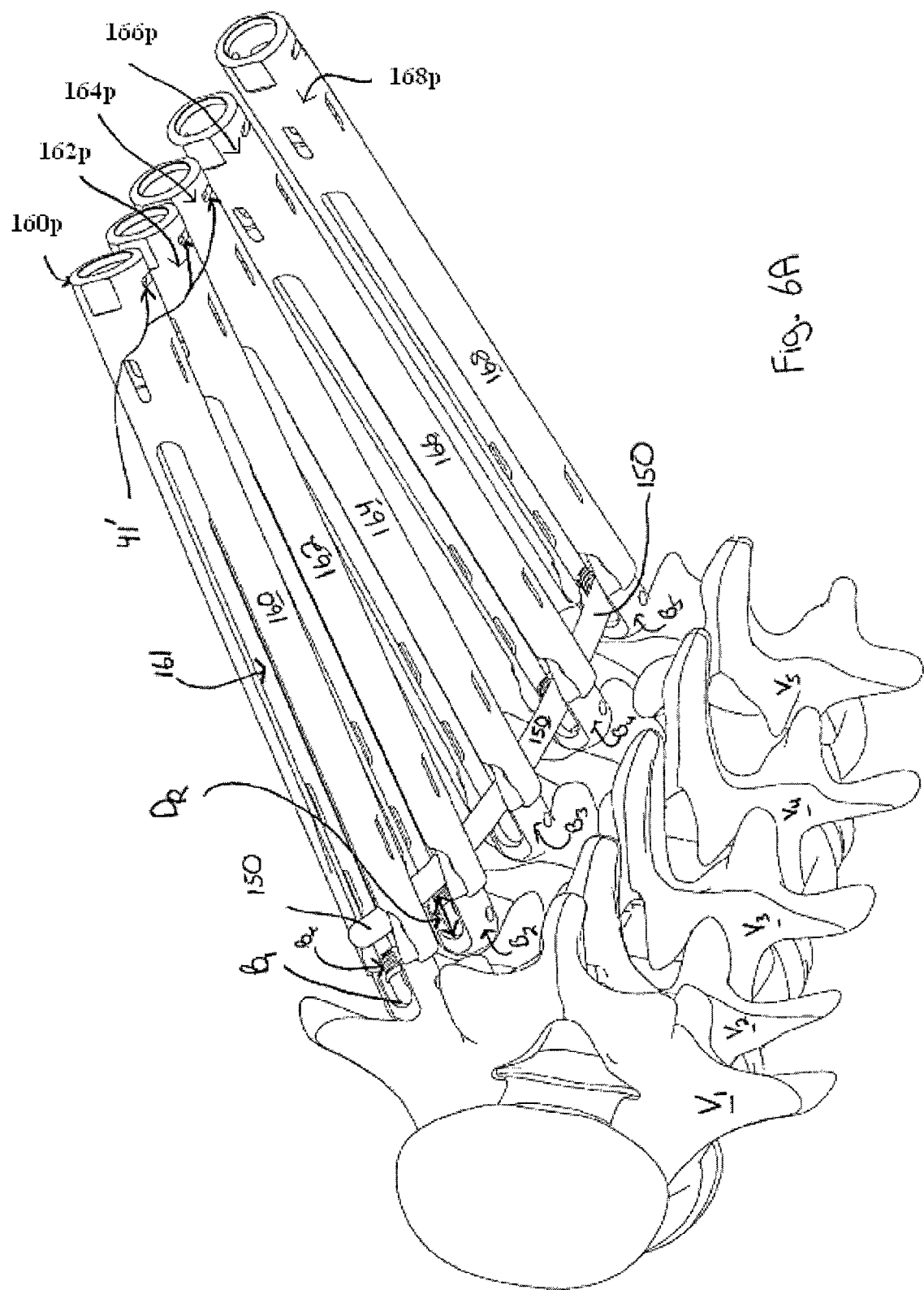
FIG. 6A is a representation of a plurality of percutaneous access devices engaged to a plurality of vertebrae.
Figure 6B:
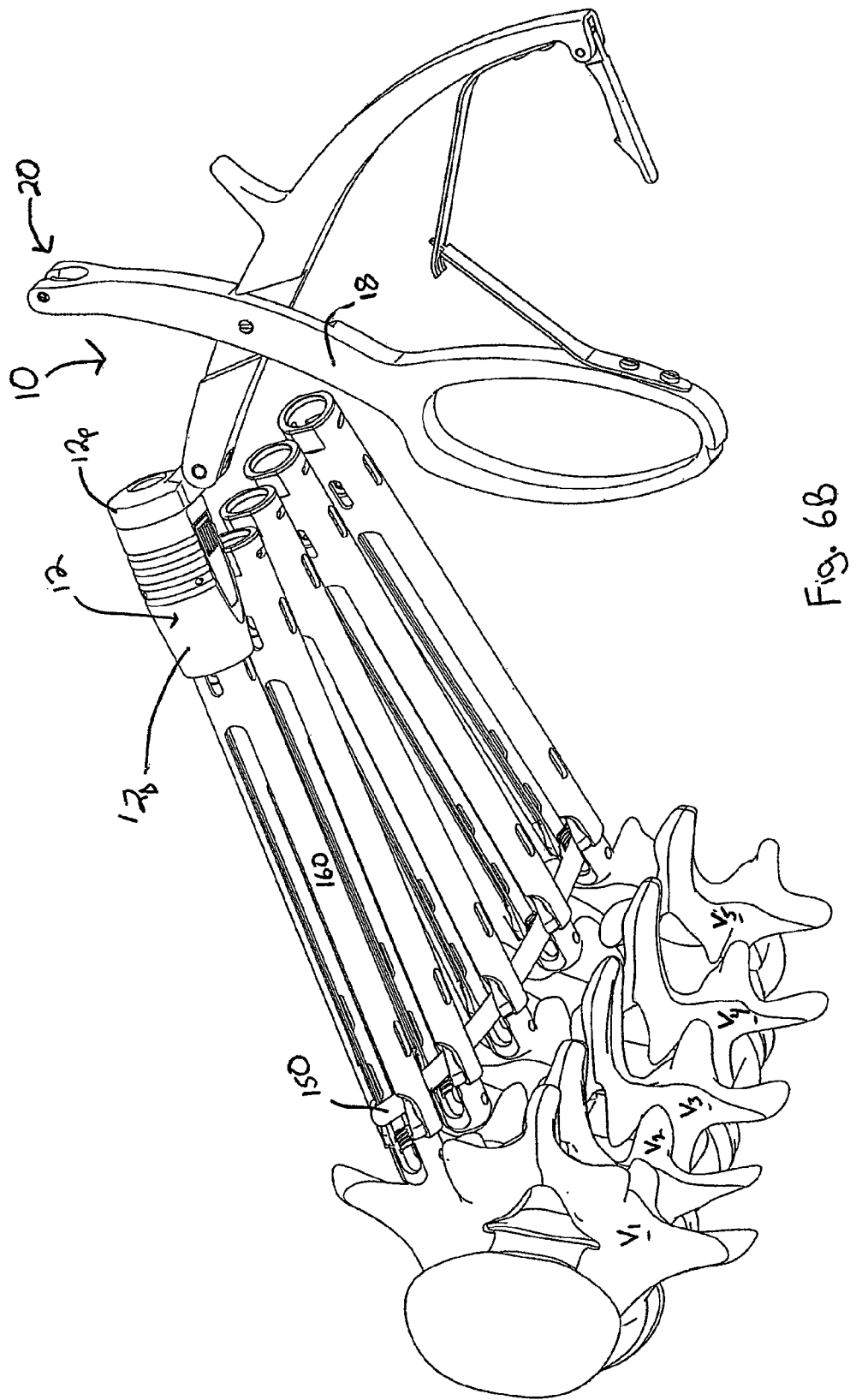
FIG. 6B is a representation of an exemplary embodiment of a drive mechanism attached to a first percutaneous access device.
Figure 6C:
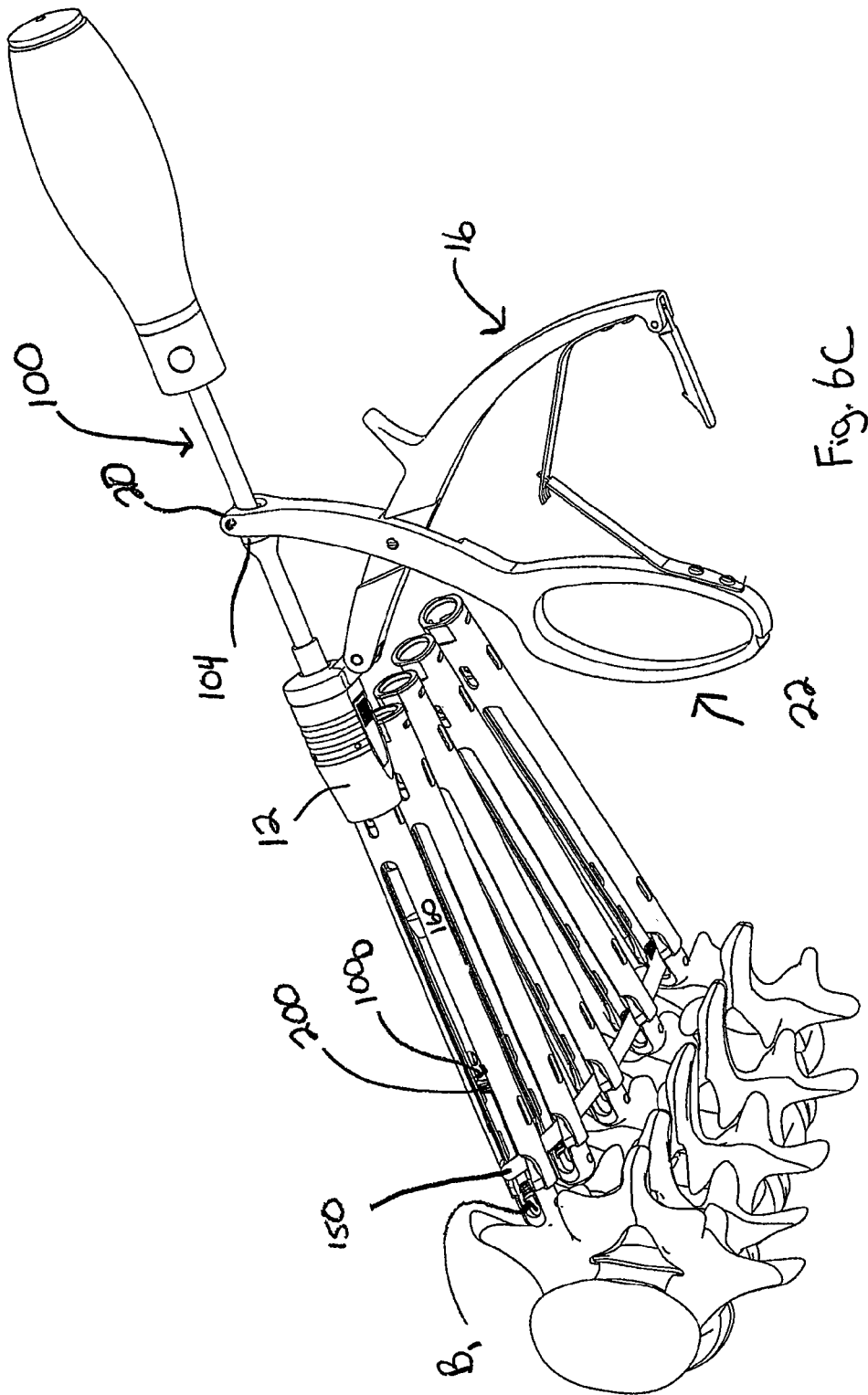
FIG. 6C is a representation of an exemplary embodiment of a driver being coupled to the drive mechanism of FIG. 6B.
Figure 6D:
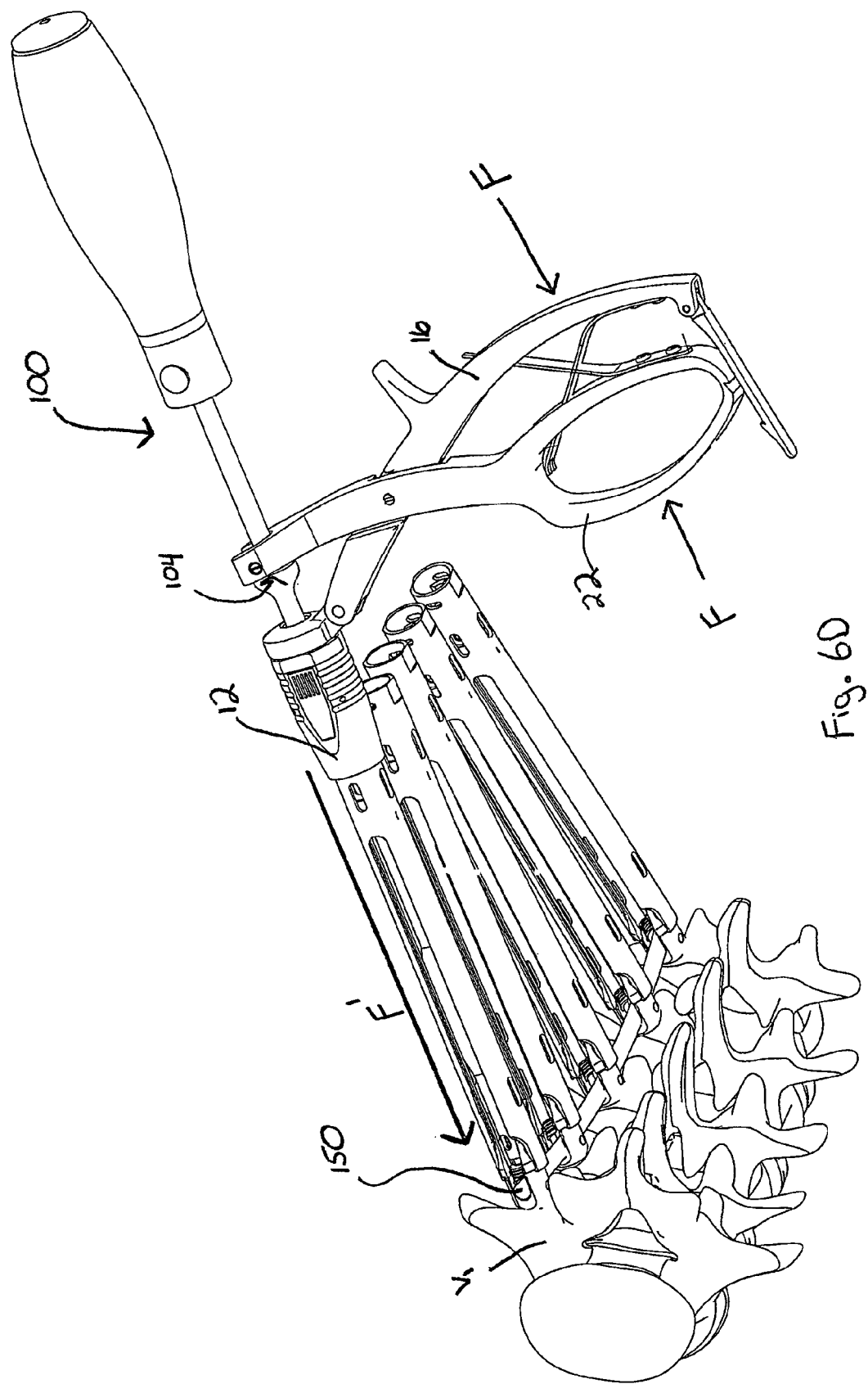
FIG. 6D is a representation of an actuation force being applied to the drive mechanism of FIG. 6C.

FIGS. 6A-6D provide an exemplary embodiment of a method in which a drive mechanism 10 can deliver a force to a driver thereby reducing a spinal fixation element 150 into a bone anchor $B_1$ that is engaged to a percutaneous access device 160. Referring to FIG. 6A, the method can include engaging a plurality of bone anchors $B_1$, $B_2$, $B_3$, $B_4$, $B_5$ to a plurality of vertebrae $V_1$, $V_2$, $V_3$, $V_4$, $V_5$ wherein the bone anchors $B_1$, $B_2$, $B_3$, $B_4$, $B_5$ are releasably engaged to a plurality of corresponding percutaneous access devices 160, 162, 164, 166, 168. As will be appreciated by those skilled in the art, each bone anchor $B_1$ can include virtually any such element configured to securely engage a vertebra $V_1$ and having a proximal portion configured to receive a spinal fixation element (e.g., a fixation rod) 150. Typically, such a bone anchor $B_1$ can include a threaded shank (not shown) polyaxially coupled to a U-shaped receiving head configured to receive a spinal fixation element 150. Further, the receiving head can also include a series of threads $B_T$ (which can be internal or external) configured to securely receive a corresponding series of threads formed on a fastening element thereby allowing the fastening element to securely retain the spinal fixation element 150 within the bone anchor $B_1$. As will be appreciated by those skilled in the art, each percutaneous access device 160, 162, 164, 166, and 168 can include any access sleeve having an inner lumen configured to provide access from a proximal end $160_P$, $162_P$, $164_P$, $166_P$, and $168_P$ thereof to the bone anchor $B_1$, $B_2$, $B_3$, $B_4$, and $B_5$. Thus, the length, size, shape, diameter, and/or configuration of the access device 160 can vary depending on the nature of the procedure and the patient's anatomy. As further shown in FIG. 6A, a spinal fixation element 150 can be disposed through a plurality of side-wall openings 161 formed in each percutaneous access device 160. However, as shown, at this stage of a typical procedure, the fixation element is generally positioned a distance $D_R$ above a corresponding bone anchor $B_2$.

Referring to FIG. 6B, an exemplary embodiment of the drive mechanism 10 can be releasably engaged a proximal portion of a percutaneous access device 160 such that a central axis of a cap element can be substantially collinear with a central axis of an inner lumen of the percutaneous access device 160. As shown, the actuator 18 can be oriented in a non-parallel manner (e.g., substantially transverse) with respect to the central axis of the bore of the cap element 12 thereby providing enhanced maneuverability for the user. Also, as described above, the ability to rotate the proximal end $12_P$ of the cap element 12 (and all components engaged thereto) relative to the releasably engaged percutaneous access device 160 further enhances the usability and maneuverability of the drive mechanism 10.

Referring now to FIG. 6C, an embodiment of a driver 100 can be slidably and removably disposed through the yoke 20 to extend through the bore of the cap element 12 and into an inner lumen of the percutaneous access device 160. In such an embodiment, the driver 100 can slide distally until a distal end $100_D$ of the driver 100 is positioned above and adjacent to the spinal fixation element 150. Further, as shown, the yoke 20 of the drive mechanism 10 can be positioned above and adjacent to a yoke interface 104 of the driver 100.

FIG. 6D shows an actuation force (F) being supplied to the actuator 18 to pivot the proximal handle portion 16 towards the grasping member 22. As described above, such an actuation force (F) causes the yoke 20 to move into contact with the yoke interface 104 thereby applying a downward force (F') along the longitudinal axis of the driver 100. As the driver 100 moves downwards, the distal end $100_D$ of the driver 100 can effect reduction of the spinal fixation element 150 into the corresponding bone anchor $B_1$. Following a successful reduction, the driver 100 can be slidably removed from the percutaneous access device 160 and a fastening element can be delivered along the percutaneous access device via an accessory surgical device. Following such delivery, the fastening element can be engaged to the proximal portion of the bone anchor B, thereby securing the spinal fixation element 150 within the bone anchor $B_1$. In another exemplary embodiment, the fastening element 200 (see FIG. 6C) can be releasably engaged to the distal end $100_D$ of the driver 100 thereby allowing the driver 100 to effect reduction of the spinal fixation element 150, secure the fastening element 200 to the corresponding bone anchor $B_1$, and disengage the distal end $100_D$ of the driver 100 from the fastening element 200. In a further embodiment of the presently disclosed method, any of the above identified steps can be repeated so as to reduce the spinal fixation element 150 into any number of additional bone anchors $B_1$, $B_2$, $B_3$, $B_4$, $B_5$, etc. extending along any desired length of the patient's spinal column.

One skilled in the art will appreciate further features and advantages of the presently disclosed system and method based on the above-described embodiments. Accordingly, the present disclosure is not to be limited by what has been particularly shown and described, except as indicated by the appended claims. All publications and references cited herein are expressly incorporated herein by reference in their entirety.

The invention claimed is:

1. A spinal fixation element reduction system, comprising:
   a cap element having a proximal end, and a distal end with a bore extending therethrough along a central axis thereof, the cap element being sized and configured to releasably engage an outer surface of a surgical sleeve wherein the cap element includes at least one selectively releasable engagement element disposed within a sidewall of the cap element and spring biased to an engagement configuration and being configured to engage the outer surface of the surgical sleeve;
   a first support having a proximal handle portion and a distal end that is pivotally coupled to the cap element; and
   an actuator pivotally attached to the first support, the actuator having a yoke at a distal portion thereof and a proximal grasping member, the actuator being effective to selectively move the yoke towards the cap element.

2. The system of claim 1, wherein the first support and the actuator are pivotally attached at intermediate portions in a scissors-like manner.

3. The system of claim 1, further comprising:
   a driver having a distal end, a proximal end, and a length extending therebetween, the driver being configured to be slidably and removably disposed through the bore of the cap element.

4. The system of claim 3, wherein the driver includes at least one marking along the length thereof, the marking configured to indicate the position of the driver relative to the cap element.

5. The system of claim 3, wherein the actuator is effective to apply a linear force to the driver along the central axis of the cap element.

6. The system of claim 5, further comprising:
   a flange element formed on a portion of the driver, the flange element having a proximal-facing surface configured to abut the yoke element as the yoke element is moved towards the cap element by actuation of the actuator.

7. The system of claim 6, further comprising:
   a pivotable member coupled to an inner surface of the yoke element to interface with the flange element, the pivotable member being configured to remain substantially flush against the proximal-facing surface of the flange element as the yoke element moves towards the cap element.

8. The system of claim 1, wherein the distal end of the cap element is configured to releasably engage the surgical sleeve, the distal portion of the cap element further being rotatably coupled to the proximal end of the cap element.

9. The system of claim 1, wherein the actuator is oriented in a non-parallel manner with respect to the central axis of the cap element.

10. The system of claim 1, wherein the actuator includes a biasing mechanism in communication with the proximal handle portion of the first support and in communication with the grasping member thereby biasing the proximal handle portion away from the grasping member.

11. The system of claim 10, wherein the biasing mechanism comprises a first prong extending from the proximal handle portion of the first support and a second prong extending from the grasping member, a distal portion of the first prong configured to engage a distal portion of the second prong.

12. The system of claim 10, further comprising:
    a locking mechanism configured to maintain a position of the proximal handle portion of the first support relative to a position of the grasping member.

13. The system of claim 1, further comprising:
    a fastening element removably attached to the distal end of the driver and configured to lock a spinal fixation element within a bone anchor.

14. The system of claim 1, wherein the distal end of the driver is effective to contact a spinal fixation element and upon distal movement of the driver along the central axis, seat the spinal fixation element within a bone anchor.

15. A modular spinal fixation element reduction system, comprising:
    a drive mechanism having a cap element, the cap element having a terminal distal end, a proximal end, and a bore extending through the cap element and having a central axis extending therethrough, the terminal distal end of the cap element being configured to releasably engage a proximal portion of a surgical sleeve;
    an engagement element disposed within a sidewall of the cap element and spring biased to an engagement configuration, the engagement element being configured to releasably engage the surgical sleeve; and
    a driver slidably configured to be removably disposed through the bore of the cap element, wherein the drive mechanism is effective to deliver a force to the driver along the central axis of the cap element thereby causing the driver to slide distally from a first position to a second position.

16. The system of claim 15, wherein the drive mechanism further comprises:

a first support having a distal portion pivotally coupled to the cap element and a proximal handle portion; and an actuator pivotally engaged to the first support such that a yoke element formed at a distal end of the actuator resides at a biased position above the cap element, the actuator further configured to allow the yoke element to pivotally move towards the cap element in response to an actuation force.

17. The system of claim 16, wherein the driver includes a yoke interface formed along a proximal portion thereof, the yoke interface configured to contact the yoke element as the yoke element pivots toward the cap element.

18. The system of claim 17, wherein the yoke interface is a flange element having a substantially planar proximal facing surface.

19. The system of claim 18, wherein the yoke element further comprises a pivotable member coupled to an inner surface thereof, the pivotable member configured to remain substantially flush with the substantially planar proximal facing surface of the yoke interface as the yoke pivots toward the cap element.

20. A spinal fixation element reduction system, comprising:

a cap element having a proximal end and a distal end with a bore extending therethrough along a central axis thereof, the cap element being sized and configured to releasably engage a surgical sleeve through a selectively releasable engagement mechanism disposed in a sidewall of the cap element that is spring biased to an engagement configuration;

a first support having a proximal handle portion and a distal end that is pivotally coupled to the cap element; and an actuator pivotally attached to the first support, the actuator having a yoke at a distal portion thereof and a proximal grasping member, the actuator being effective to selectively move the yoke towards the cap element.

* * * * *